United States Patent [19]

Margolis et al.

[11] Patent Number: 4,474,471
[45] Date of Patent: Oct. 2, 1984

[54] CORRELATION SPECTROMETER HAVING HIGH RESOLUTION AND MULTIPLEXING CAPABILITY

[75] Inventors: Jack S. Margolis, Pasadena; John V. Martonchik, Burbank, both of Calif.

[73] Assignee: The United States of America as represented by the Administrator of the National Aeronautics and Space Administration, Washington, D.C.

[21] Appl. No.: 373,770

[22] Filed: Apr. 30, 1982

[51] Int. Cl.³ .......................................... G01N 21/59
[52] U.S. Cl. .................................... 356/434; 250/343; 250/351; 356/51
[58] Field of Search ................. 356/51, 432, 434, 436, 356/437; 250/343, 351

[56] References Cited

U.S. PATENT DOCUMENTS

| | | | |
|---|---|---|---|
| 3,658,422 | 4/1972 | Wilkinson | 356/321 |
| 3,694,086 | 9/1972 | May | 356/51 |
| 3,723,731 | 3/1973 | Blau, Jr. | 356/51 X |
| 3,744,918 | 7/1973 | Jacobson | 356/324 |
| 3,853,407 | 12/1974 | Dewey, Jr. | 359/419 |
| 4,070,111 | 1/1977 | Harrick | 356/308 |
| 4,094,608 | 6/1978 | Young | 356/326 |
| 4,105,919 | 8/1978 | Bridges et al. | 250/341 |
| 4,169,678 | 10/1979 | Inoue et al. | 356/321 |

OTHER PUBLICATIONS

Herget et al., *Applied Optics*, vol. 15, No. 5, May 1976, pp. 1222–1228.

Primary Examiner—F. L. Evans
Attorney, Agent, or Firm—Paul F. McCaul; Thomas H. Jones; John R. Manning

[57] ABSTRACT

A correlation spectrometer permanently incorporates a reference cell (12) and an electro-optical phase modulator (EOPM) (50) in the light path between a sample cell (30) and a detector (20). The effect of the EOPM is such that its frequency modulates all of the monochromatic component of the incoherent radiation passing through it. The EOPM is adjusted so that when it is ON all of the energy in the monochromatic components is thrown into sidebands (55) differing from the original frequencies by integral multiples of the modulation frequency, with the total amount of energy absorbed from the original radiation remaining constant. When there is no coincidence between the constituents in the two cells, the detector's output is the same when the EOPM is ON and when it is OFF. However, when there is coincidence the detector's output changes when the EOPM is switched between its two states. The change in the detector's output is related to the quantity of the constituents in the sample cell.

10 Claims, 10 Drawing Figures

FIG. 1
PRIOR ART
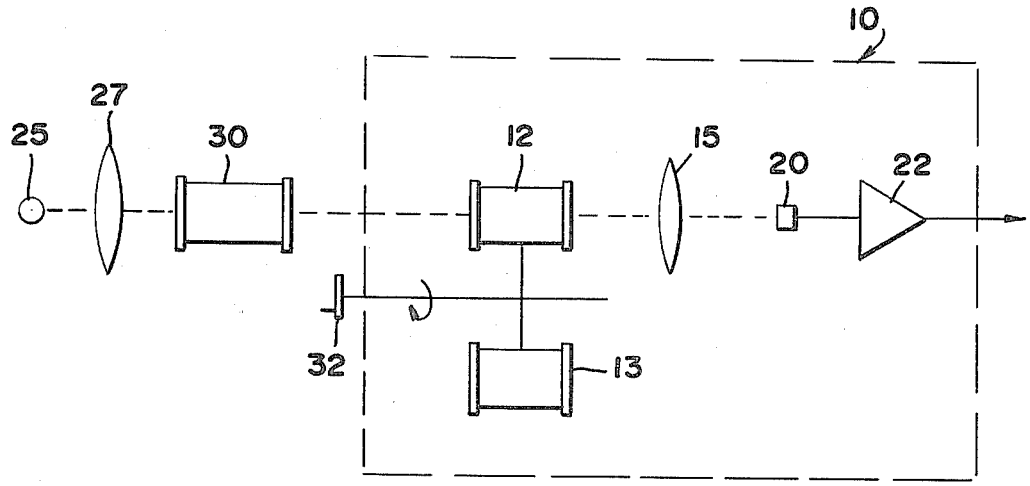
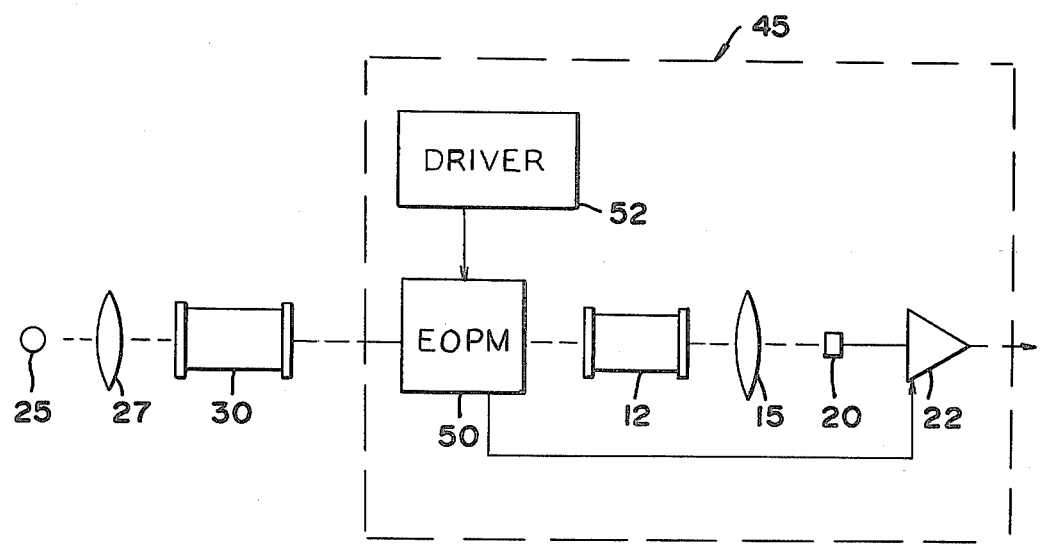
FIG. 3

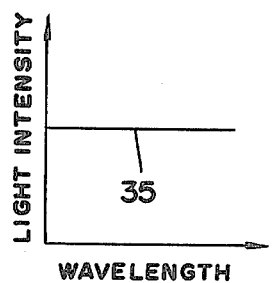
FIG.2a
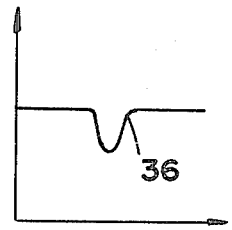
FIG.2b
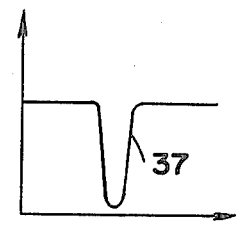
FIG.2c
FIG.2d
FIG.2e
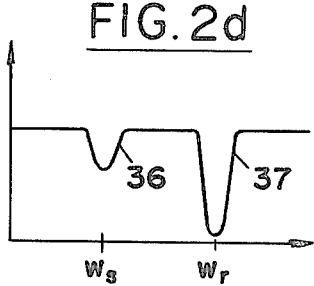
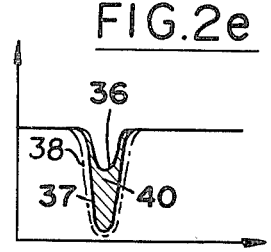
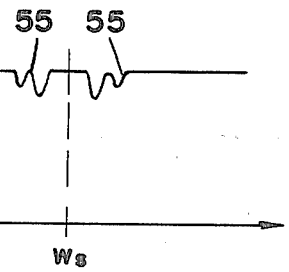
FIG.4
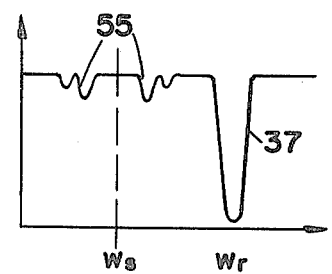
FIG.5
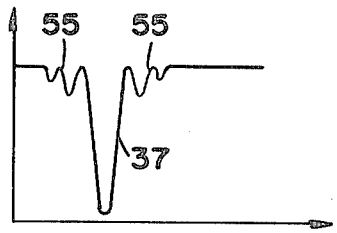
FIG.6

CORRELATION SPECTROMETER HAVING HIGH RESOLUTION AND MULTIPLEXING CAPABILITY

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 USC 2457).

BACKGROUND OF THE INVENTION

1. Field of the Invention

The present invention generally relates to a correlation spectrometer and, more particularly, to a correlation spectrometer with an electro-optical phase modulator.

2. Description of the Prior Art

Herebefore, a correlation spectrometer, used to determine the presence of one or more molecular constituents in a sample cell and their amounts, utilized a reference cell which was physically interchangeable with an empty cell, in the path of light between the sample cell and the detector. The need for mechanical interchanging of the empty cell and the reference cell in the light path has been found to be quite disadvantageous. It creates alignment and stability problems which often affect the accuracy of the measurements. Other prior correlation spectrometers use different arrangements, such as a reflecting chopper which switches a beam, a Luft cell, and a pressure modulated radiometer (PMR). With these known prior art arrangements, the measurements are often subject to sensitivity and stability limitations and to noise.

A need therefore exists for a new correlation spectrometer in which the physical interchanging of cells in the light path is eliminated. Furthermore, a need exists for a stable, sensitive correlation spectrometer with which accurate measurements of the quantities of constituents, detected to be present in the sample cell, are achievable.

OBJECTS AND SUMMARY OF THE INVENTION

A primary object of the present invention is to provide a new improved correlation spectrometer.

Another object of the present invention is to provide a correlation spectrometer which eliminates the need for physically interchanging empty and reference cells.

A further object of the present invention is to provide a correlation spectrometer, capable of providing precise measurements of quantities of detected constituents in the sample cell.

These and other objects of the present invention are achieved with a correlation spectrometer which permanently incorporates a reference cell in the light path between the sample cell and the detector and further permanently incorporates an electro-optical phase modulator, which can be switched to be ON or OFF, and which is located between the sample and reference cells. To simplify the following description, it will be assumed that the reference cell contains a single known constituent, representable by a single absorption line and that the quantity of the constituent is large so that the reference cell absorption line is quite strongly absorbing, and that the sample cell may contain only one constituent, representable by a single absorption line, which may or may not be the same as that in the reference cell.

The operation of the electro-optical phase modulator (EOPM) will be described hereafter in detail. However, for summary purposes it is sufficient to state that the EOPM is adjustable so that when it switches ON it modifies the sample cell absorption line by transferring all or some of that absorption into adjacent frequencies or sidebands. When the EOPM is OFF, the sample cell absorption line is unaffected.

In operation, when there is no coincidence between the contents of the sample and reference cells, the light incident on the detector and therefore its electrical output is the same when the EOPM is OFF or ON. On the other hand, when coincidence is present, the light, incident on the detector, is less when the EOPM is ON than when it is OFF. This difference is an exact measurement of the quantity of the constituent, coincident with that in the reference cell, which is present in the sample cell.

The novel features of the invention are set forth with particularity in the appended claims. The invention will be best understood from the following description when read in conjunction with the accompanying drawings.

BRIEF DESCRIPTION OF THE DRAWINGS

FIG. 1 is a diagram useful in explaining a Prior Art correlation spectrometer;

FIGS. 2a–2c are diagrams of light spectra through an empty cell, a sample cell and a reference cell respectively;

FIG. 2d is a diagram of light spectrum through both sample and reference cells in the prior art spectrometer in the absence of coincidence;

FIG. 2e is a diagram of the light spectrum through the sample and reference cells in the prior art spectrometer when there is coincidence as well as in the present invention when there is coincidence and the electro-optical phase modulator is OFF;

FIG. 3 is a diagram of the novel correlation spectrometer in accordance with the present invention;

FIG. 4 is a diagram of the light spectrum through the sample cell and the EOPM; and FIGS. 5 and 6 are diagrams of light spectra when the modulator is ON, when there is no coincidence of the contents with sample and reference cells, and when there is coincidence, respectively.

DETAILED DESCRIPTION OF THE DRAWINGS

Attention is first directed to FIG. 1 which is a simplified diagram of a prior art correlation spectrometer. The prior art will be summarized so as to more clearly highlight the advantages of the present invention. In FIG. 1, the correlation spectrometer is designated by numeral 10 and is shown to include reference cells 12, an empty cell 13, a condensing lens 15, and a light detector 20, whose output is amplified by a lock-in amplifier 22. Light from a source 25 is collimated by a lens 27 and passes to the correlation spectrometer 10 through a sample cell 30, the contents of which is being analyzed both qualitatively and quantitatively. In operation, the reference cell 12 and the empty cell 13 are physically interchanged in the light path. The cell interchanging is generally achieved by a mechanical cell-rotating mechanism, designated by numeral 32. As previously pointed out the need to physically interchange cells in the correlation spectrometer is quite undesirable for reasons herebefore stated.

Attention is now directed to FIGS. 2a-2e which are spectrums of light intensity vs. wavelength (w) useful in explaining the prior art. FIG. 2a is the spectrum of the empty cell 13, represented by the straight line 35, since cell 13 is empty and therefore nothing therein absorbs light. FIGS. 2b and 2c respectively represent the spectra in the sample cell 30 and the reference cell 12 by the single absorption lines 36 and 37, based on the assumption that each contains a single constituent. Furthermore, the reference cell is assumed to contain enough of the constituent to practically totally absorb the light and therefore absorption line 37 is much stronger than that of absorption line 36.

When the empty cell 13 is in the light path, the total spectrum as observed by the detector is the same as that shown in FIG. 2b for the sample cell, since light is not absorbed in the empty cell.

However, when the reference cell 12 is placed in the light path, the composite spectrum depends on whether or not there is coincidence, i.e. identity between the constituents in the sample and reference cells. If there is no coincidence, the composite spectrum is as shown in FIG. 2d, in which lines 36 and 37 do not coincide. Thus, light, at wavelengths $w_s$ and $w_r$, is absorbed, where the subscripts s and r refer to the sample and reference cells, respectively. On the other hand, when coincidence is present, the total composite spectrum is as shown in FIG. 2e. Due to the fact that the reference cell has been adjusted to be practically totally absorbing, the sample cell absorption line 36 is within the reference cell line 37, and therefore is not observable at the detector. In FIG. 2e the difference between the absoprtion line 36 (of the sample cell) and line 38 which represents the net transmission through both the sample and reference cells) is designates by the cross-hatched area 40. The size of the cross-hatched area 40 depends on the quantity of the constituent in the sample cell-the greater the quantity the smaller the area.

In order to quantitatively determine the amount of constituent in the sample cell the correlation spectrometer must first be calibrated by determining the signal strength, corresponding to no constituent in the sample cell, and then subtracting this from the measurements. Small variations in this subtraction process or in the optical balance of the spectrometer can strongly affect the quantitative determination of the sample amount.

Unlike the prior art correlation spectrometer and the measurements that have to be performed by its use, in accordance with the present invention, a correlation spectrometer 45, as shown in FIG. 3, is provided. In FIG. 3, elements like those previously described are designated by like numerals. In the novel correlation spectrometer 45, the reference cell 12 is permanently placed in the light path. Thus, the need for the empty cell 13 and the cell-positioning mechanism 32 is eliminated. The spectrometer 45 includes an electro-optical phase modulator (EOPM) 50 which is permanently positioned in the light path between the sample cell 30 and the reference cell 12, and which is switched ON and OFF by a driver 52. EOPM 50 supplies a reference signal to lock in amplifier for synchronization purposes.

When the EOPM is OFF, it does not affect the absorption spectrum of the sample cell (as shown in FIG. 2b by line 36) as seen by the reference cell. However, when the EOPM is switched ON, a significant change in the light absorption spectrum which passes therethrough occurs. For the specific example, the amplitude of the modulation due to the EOPM 50 is adjustable so that when it is ON, it completely suppresses the sample absorption line 36 and produces an absorption pattern as shown in FIG. 4 and designated by numerals 55. Considering the frequencies in the sample absorption line 36 as carriers, the EOPM 50 suppresses these carriers totally, and produces a spectrum of positive and negative sidebands 55, of a total absorption, equal to that of the suppressed carrier or line 36.

The advantages realizable with the novel spectrometer 45 with EOPM 50 may best be explained in connection with the following figures. When the EOPM 50 is OFF, it does not affect the sample line 36. Thus, if there is no coincidence the total spectrum is as shown in FIG. 2d with lines 36 and 37 not coinciding. Then, when EOPM 50 is turned ON and there is no coincidence, the total spectrum is as shown in FIG. 5, with the sidebands 55 not coinciding with the reference line 37. However, since the energy in the sidebands 55 is the same as that in the sample line 36, the light incident on the detector is the same for the spectrum shown in FIG. 2d where there is no coincidence and EOPM 50 is OFF, and for the spectrum of FIG. 5, where there is no coincidence and EOPM 50 is ON. Thus, if there is no coincidence, the detector output is the same when EOPM 50 is OFF or ON.

A significant, very precise difference in the detection output takes place when there is coincidence. Under such a condition, when EOPM 50 is OFF, the sample line 36 is not affected by the EOPM and it coincides with the reference line 37, as shown in FIG. 2e. Thus, the total spectrum is very nearly as if only the reference cell were in the light path. However, when EOPM 50 is turned ON (and coincidence is present) the total spectrum is as shown in FIG. 6. That is, the reference line 37 is between sidebands 55, without any overlapping.

When comparing the spectrum of FIG. 2e, which represents coincidence, with EOPM OFF, and the spectrum of FIG. 6, which represents coincidence with EOPM OFF, it is seen that the light incident on the detector is different when EOPM 50 is OFF, or ON, and there is coincidence. In fact, the difference is related to the energy in the sidebands which is directly related to the quantity of the constituent in the sample cell 30.

From the foregoing, it should thus be appreciated that in the spectrometer 45, when there is no coincidence, the output is the same whether EOPM 50 is ON or OFF. Thus, the absence of output change indicates absence or coincidence. If, however, the output differs for EOPM 50 being OFF or ON, it indicates coincidence, thus identifying the constituent in the sample cell 30 as being the same as the known constituent in the reference cell. As to the quantity of the constitutent, in the sample cell, it is directly related to the change in the output of the spectrometer when EOPM 50 is OFF and when it is ON.

The operations of electro-optical modulators, such as EOPM 50, incorporated in the present invention, are well understood and are described in several texts. One of these texts is entitled "Introduction to Optical Electronics" by A. Yariv, published by Holt, Rinehart and Winston, Inc. in 1971. Section 9.4 is of particular interest. Different electro-optical modulators in the different regions of the spectrum are available commercially. For example, for use in the 8–12 $\mu m$ region, a CdTe crystal is presently believed to be the best electro-optical material. When a voltage V is connected across a properly oriented crystal, the incident infrared beam is phase modulated. For 43 crystals such as CdTe, the applied voltage should be perpendicular to the (111) planes and the propagation of the beam can be along any axis in the (111) plane.

The amount of phase delay $\delta$ due to the electrooptic effect is, $$\delta = -\frac{2n_o^3 r_{41} V}{3W}\left(\frac{l}{d}\right) \text{ for polarizations parallel to V}$$

$$\delta = \frac{\pi n_o^3 r_{41} V}{3W}\left(\frac{l}{d}\right) \text{ for polarizations perpendicular to V}.$$

where
$l$ = crystal length
$d$ = crystal height $W$ = IR wavelength $n_o^3 r_{41} = 1.2 \times 10^{-10}$ m/V for $CdTe$ where
l = crystal length
d = crystal height
W = IR wavelength
$n_o^3 r_{41} = 1.2 \times 10^{-10}$ m/V for CdTe If the applied voltage is $V \cos \omega_m t$, the output IR beam is phase modulated at frequency $\omega_m$ and the IR electric field, $\epsilon'$, can be written as a series of upper and lower sidebands or sidelobes, $$\epsilon' = A\left\{ J_o(\delta)\cos\omega t + \sum_{n=1}^{\infty} [J_n(\delta)\cos(\omega + n\omega_m)t + (-1)^n J_n(\delta)\cos(\omega - n\omega_m)t] \right\}$$

where $\omega$ is the incident IR frequency and $J_n(\delta)$ are Bessel functions. Thus, the output is a series of lines equally spaced with intervals $\omega_m$ above and below the input W. The amplitude of the sidebands depends on $\delta$ and hence on V. Thus, the spacing and the amplitude of the sidebands are electronically controllable. It should be noted that if $\delta = 2.33$, $J_o(2.33) = 0$, all of the power is in the sidebands. The above holds true for emission or absorption lines.

For efficient operation, it is required that the modulation frequency be greater than the width of the absorption line. For example, for atmospheric molecules the Doppler half width is 30 MHz at W=10 $\mu$m. This implies that $W_m$=50 MHz which is a sufficient modulation frequency for probing into the stratosphere and for laboratory operation at low sample gas pressure.

Although herebefore the correlation spectrometer has been described incorporating the EOPM, the broad aspects of the invention are not intended to be limited thereto. For example, a high frequency amplitude modulator may also be employed. One example of a well known frequency amplitude modulator is the Kerr cell. Although it may require some additional optical elements its spectral complexity is reduced in that only two sidebands are produced, an upper and lower, displaced from the central frequency by the modulation frequency.

Although particular embodiments of the invention have been described and illustrated herein, it is recognized that modifications and variations may readily occur to those skilled in the art and consequently, it is intended that the claims be interpreted to cover such modifications and equivalents.

What is claimed is:

1. For use in a correlation spectrometer of the type to which light, after passing through a sample cell which may contain light-absorbing matter, is directed and which includes a light-sensitive detector, an arrangement comprising:
   a reference cell containing preselected matter and of a selected quantity, said reference cell being fixedly positioned in the light path between said sample cell and said detector;
   an electro-optical phase modulator fixedly positioned in the light path between said sample and reference cell; and
   control means coupled to said electro-optical modulator for switching said modualtor between an OFF state, in which the light spectrum from said sample cell passes through said electrooptical modulator undisturbed, and an ON state, wherein any absorption lines in the light spectrum from said sample cell are substantially suppressed and pass said electro-optical modulator as sidelobes' absorption patterns.

2. For use in a correlation spectrometer as described in claim 1 wherein said control means control said electro-optical phase modulator to substantially fully suppress each absorption line in the sample cell's light spectrum and replace it with sidelobes' absorption patterns of equal energy.

3. For use in a correlation spectrometer as described in claim 1 wherein said control means control said electro-optical phase modulator so that when the sample cell does not contain matter corresponding to that in the reference cell, definable as lack of coincidence, the detector output is substantially the same when said electro-optical phase modulator is in either its OFF or ON state, and when coincidence is present, the difference between the outputs of the detector, when said electro-optical phase modulator is either ON or OFF, is related to the amount of matter in said sample cell.

4. For use in a correlation spectrometer as described in claim 3 wherein said control means control said electro-optical phase modulator to substantially fully suppress each absorption line in the sample cell's light spectrum and replace it with sidelobes' absorption patterns of equal energy.

5. For use in a correlation spectrometer as described in claim 3 wherein the quantity of matter in said reference cell is not less than any expected quantity of like matter which may be present in said sample cell.

6. For use in a correlation spectrometer as described in claim 5 wherein said control means control said electro-optical phase modulator to substantially fully suppress each absorption line in the sample cell's light spectrum and replace it with sidelobes' absorption patterns of equal energy.

7. An arrangement for detecting the presence or absence of coincidence between matter contained in a reference cell and any matter containable in a sample cell, and for further detecting, when coincidence is present, the quantity of matter in said sample cell, the arrangement comprising:
   a source of light;

means for passing said light through said sample cell so that light may be absorbed by matter in said sample to produce a light spectrum which is dependent on the quality and quantity of matter in said sample cell;

a light sensitive detector in the path of the light exiting said sample cell;

a reference cell containing a predetermined quantity of predetermined matter, positioned in the light path exiting said sample cell; and electro-optical phase modulator means between said sample and reference cells, said electro-optical modulator means being switchable between an OFF state wherein the light absorption spectrum out of said sample cell passes to said reference cell undisturbed, and an ON state wherein any absorption line in the light absorption spectrum from said sample cell is suppressed and represented in said spectrum by sidelobes' absorption patterns.

8. A method of spectrometrically correlating at least the type of any matter in a sample cell with matter of known type and quantity in a reference cell, the steps comprising:

passing light through said sample cell whereby the light absorption spectrum exiting said sample cell is related to any matter containable in said sample cell and the quantity thereof;

directing the light, with said light absorption spectrum, which passed said sample cell to a light-sensitive detector;

fixedly positioning in the light path between said sample cell and that said detector a reference cell containing a known quantity of known matter;

fixedly positioning in the light path between said sample and reference cells an electro-optical phase modulator; and controlling said electro-optical phase modulator; to switch between OFF and ON states, so that when the sample cell does not contain matter present in the reference cell, definable as lack of coincidence, the detector's output is the same when the modulator is in either state, and when the detector's output differs between the OFF and ON states of said electro-optical modulator it indicates coincidence.

9. A method of spectrometrically correlating at least the type of any gaseous matter in a sample cell as recited in claim 8 wherein the quantity of the matter in said reference cell is sufficiently large to fully absorb the light passing through said reference cell at a frequency related to said matter.

10. A method of spectrometrically correlating at least the type of any matter in a sample cell as recited in claim 9 wherein the electro-optical phase modulator is controlled so that when there is a difference in the detector output when the electro-optical phase modulator is OFF and when it is ON, thereby indicating coincidence between matter in the two cells, the difference is related to the quantity of matter in said sample cell.

* * * * *